United States Patent
Ishida et al.

(12)

(10) Patent No.: US 6,355,627 B1
(45) Date of Patent: Mar. 12, 2002

(54) BRANCHED CYCLODEXTRIN CLATHRATE COMPOUND OF HINOKITIOLS AND COMPOSITION CONTAINING THE SAME

(75) Inventors: Kenya Ishida; Kazutoshi Sakurai, both of Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 09/244,106

(22) Filed: Feb. 4, 1999

(51) Int. Cl.[7] ............................................. A61K 31/715
(52) U.S. Cl. ......................... 514/58; 536/46; 536/103; 512/2; 512/3; 512/4
(58) Field of Search ....................... 512/2, 3, 4; 536/16, 536/103; 514/58

(56) References Cited

U.S. PATENT DOCUMENTS 5,024,998 A * 6/1991 Bodor .......................... 514/58
5,730,969 A * 3/1998 Hora et al. ................. 424/85.1
5,811,114 A * 9/1998 Knight et al. .................. 536/54
5,955,093 A * 9/1999 Woo et al. .................. 424/401

FOREIGN PATENT DOCUMENTS

EP          0 822 447 A1     12/1998

* cited by examiner

*Primary Examiner*—James O. Wilson
(74) *Attorney, Agent, or Firm*—Sughrue Mion, PLLC

(57) ABSTRACT

The invention has an object of providing a hinokitiol which is not damaged in the antibacterial activity and improved in the water solubility, heat stability (anti-sublimation characteristics) and corrosion to metals and also providing a composition comprising a hinokitiol. The invention resides in a clathrate compound comprising clathration of hinokitiols by using a branched cyclodextrin such as a branched β-cyclodextrin. The clathrate compound can be used in various applications requiring an antibacterial activity, such as hair cosmetics, bath agents, skin cosmetics and oral compositions.

14 Claims, 5 Drawing Sheets

BRANCHED CYCLODEXTRIN CLATHRATE COMPOUND OF HINOKITIOLS AND COMPOSITION CONTAINING THE SAME

BACKGROUND OF THE INVENTION

1. Field of the Invention

The present invention relates to a clathrate compound of hinokitiol or a metal salt of hinokitiol and to a composition containing the clathrate compound.

2. Prior Art

Hinokitiols have a high antibacterial activity against various Gram-positive bacteria and Gram-negative bacteria and have been known to exhibit an antibacterial activity against mesitylene-resistant staphylococcus aureus (MRSA) in recent years. By using the characteristics of a hinokitiol based on its antibacterial activity, it is utilized in various applications such as medicament, fragrant cosmetic and food fields.

However, hinokitiols have the drawbacks of high sublimation, deficient thermal stability and strong corrosiveness to metals, e.g., stainless, as well as poor solubility in water.

For this, trials for water-solubilization of hinokitiols have been made and clathrate compounds of disbranched cyclodextrins (hereinafter described as "disbranched CD" as the case may be) have been proposed (Japanese Patent Application Publication (JP-B) No. 1-53,856). However, the solubilities of clathrates of disbranched CD in water at 15° C. are 13 g/100 ml in the case of α-CD clathrates containing 38 mol% of a hinokitiol, 0.3 g/100 ml in the case of β-CD clathrates containing 92 mol% of a hinokitiol and 0.9 g/100 ml in the case of γ-CD clathrates containing 60 mol% of a hinokitiol. The solubility of each clathrate including the β-CD clathrate is insufficient. Moreover, hinokitiols have a solubility insufficient to be formulated into fragrant cosmetics, health and sanitary materials or medicaments.

SUMMARY OF THE INVENTION

Present inventors have conducted various studies to solve the above problems and as a result found that the solubilities of hinokitiols in water, fragrant cosmetics, health and sanitary materials and medicaments can be improved in contrast with clathrates of disbranched CD without damaging the antibacterial activity of a hinokitiol by clathration of hinokitiols by using branched cyclodextrin (hereinafter described as "branched CD" as the case may be). The present inventors have also found that the sublimation, the corrosive characteristics and the like of a hinokitiol can be improved and the invention was thus completed.

According to a first aspect of the present invention, there is provided a clathrate compound comprising clathration of hinokitiols by using a branched cyclodextrin.

In preferred embodiments, the hinokitiols are at least one compound selected from the group consisting of a hinokitiol and a metal salt of hinokitiol;

the branched cyclodextrin is a branched β-cyclodextrin; and the clathrate compound is a water-soluble powder.

According to another aspect of the present invention, there is provided a composition comprising the clathrate compound.

In preferred embodiments, the composition comprising the clathrate compound has an antibacterial activity; and the composition comprising the clathrate compound is a composition selected from the group consisting of a cosmetic composition, a bath agent, a detergent and an oral composition.

BRIEF DESCRIPTION OF THE DRAWINGS

In the accompanying drawings, there are shown illustrative embodiments of the invention from which these and other of its objectives, novel features, and advantages will be readily apparent.

In the drawings.

DETAILED DESCRIPTION OF THE INVENTION

Figure 1:
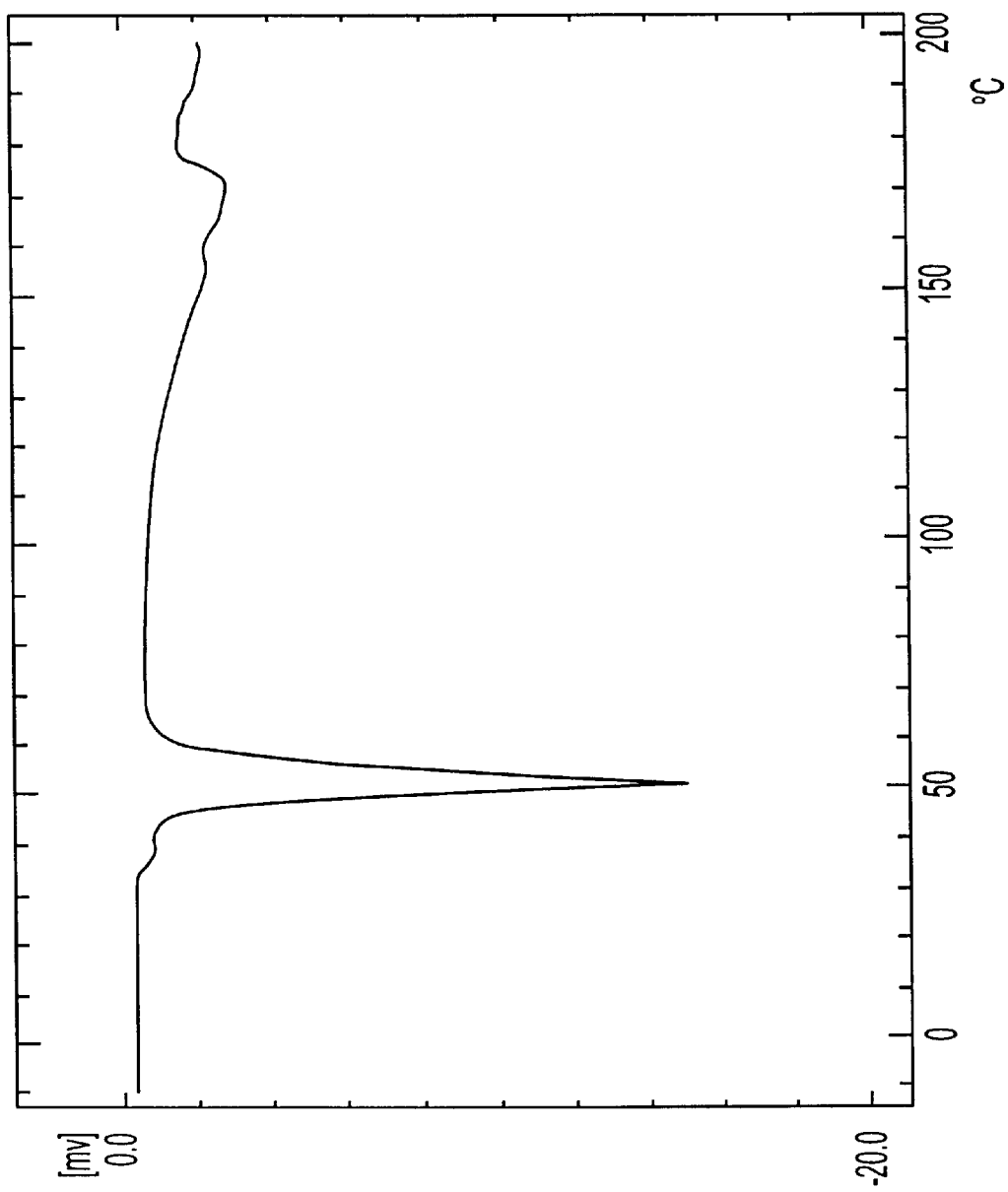
FIG. 1 is an analysis graph showing the result of a differential thermal analysis of a hinokitiol.
Figure 2:
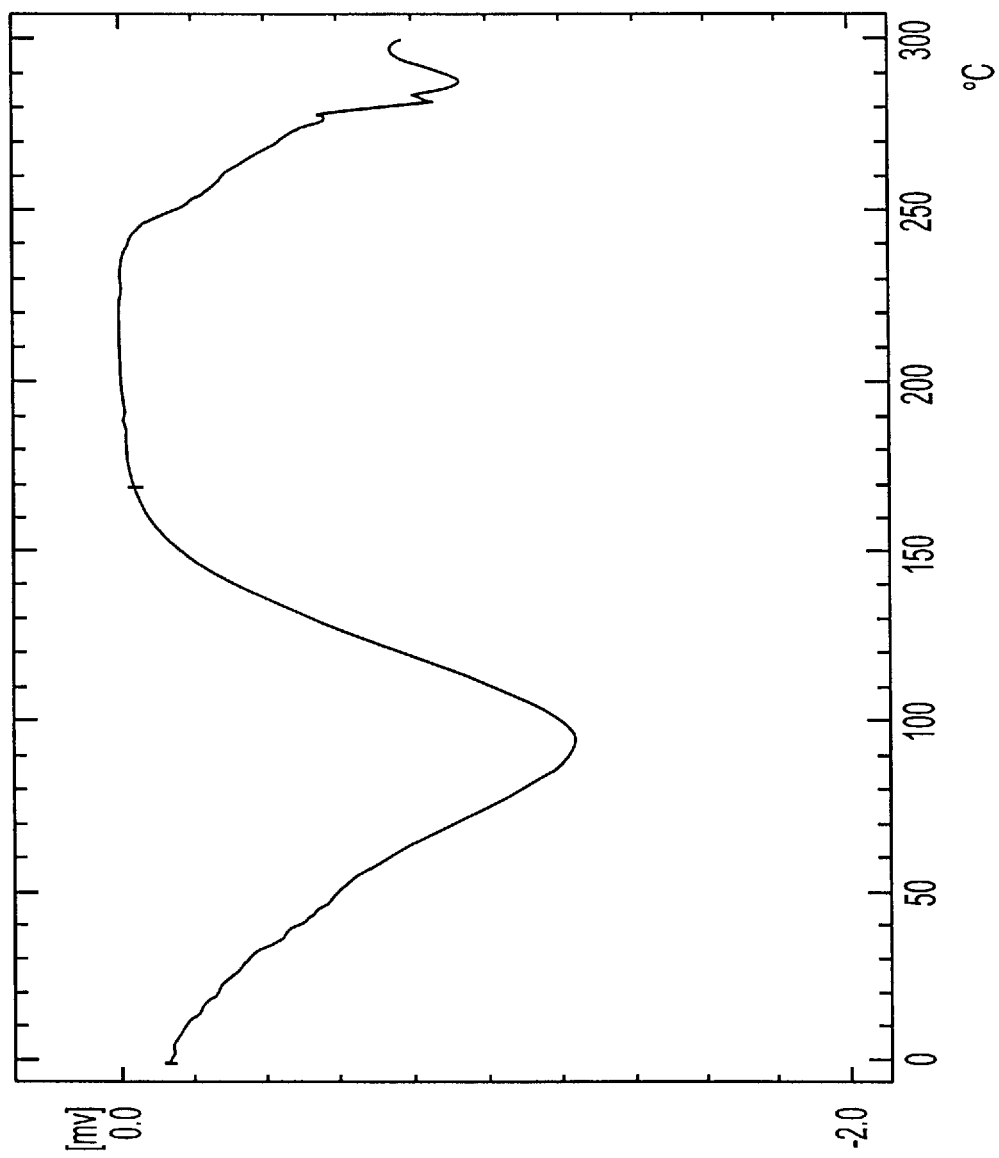
FIG. 2 is an analysis graph showing the result of a differential thermal analysis of a $G_1$-β-CD.

The present invention will be explained in detail.

Examples of hinokitiols include, other than a hinokitiol, its metal salts such as sodium, potassium, magnesium, calcium, barium, aluminum, zinc, copper, and silver salts.

The branched CD in the present invention are those having the structure in which one or two molecules of an oligosaccharide such as glucose, maltose and maltotriose are bound with a CD such as an α-CD, β-CD, or γ-CD at a-1,6 positions. Those having the structures in which one and two glucose molecules are bound are called "glucosyl CD" (hereinafter abbreviated as "$G_1$-CD") and "diglucosyl CD" (hereinafter abbreviated as "$G_1$-$G_1$-CD") respectively. Likewise, those having the structures in which one and two maltose molecules are bound are called "maltosyl CD" (hereinafter abbreviated as "$G_2$-CD") and "dimaltosyl CD" (hereinafter designated as "$G_2$-$G_2$-CD") respectively. In the present invention, preferred examples of the branched CD include branched β-CDs such as a $G_1$-β-CD and $G_2$-β-CD. These branched CDs may be used either singly or in combinations of two or more.

The clathrate compound of the present invention can be produced by bringing the branched CD into contact with at least one compound selected from a hinokitiol and its metal salts in the presence of water to produce a clathrate compound of the hinokitiols and branched CD and, as required, by drying and powdering the resulting clathrate compound. The above contact operation is generally performed by dissolving the branched CD in water, adding the hinokitiols to the solution and stirring or shaking the mixture vigorously for several seconds to several hours by using a stirrer, homogenizer or the like. Further possible clathration methods include a method of shaking the above components in a closed container and a method of treating the above components ultrasonically. The hinokitiols may be added either in the form of a crystal as it is or in the form of a solution produced by dissolving in an organic solvent.

Given as examples of the organic solvent are acetone, ethanol and methanol, in which acetone is most preferable. There are no limitations to the amount of the organic solvent as long as it can dissolve hinokitiols. The amount of the hinokitiols is generally 0.1 to 1 equivalent mol and preferably 0.5 to 1.0 equivalent mol based on the branched CD.

The contact reaction temperature is generally 0 to 60° C. and preferably 5 to 35° C.

The resulting clathrate compound is dried and powdered as it is thereby producing a clathrate compound powder containing the hinokitiols.

The fact that the clathrate compound of the present invention is not a simple mixture but forms a clathrate can be confirmed by a differential thermal analysis using a differential scanning calorimeter (DSC) and by a measuring method using a nuclear magnetic resonance instrument (NMR)

The branched CD clathrate compound of hinokitiol prepared in the present invention may be used in various forms, for example, in the form of a powder or solution as it is.

The branched CD clathrate compound of hinokitiol prepared in the present invention must be varied in its concentration to be adaptable to the proper range according to the types and object of products to which an antibacterial activity is to be imparted. The clathrate compound of the present invention is used in a concentration of generally 0.01 to 10% by weight and preferably 0.1 to 5% by weight based on the total amount of all components of the product.

In the object product compositions to which the clathrate compound of the present invention is applied, optional components corresponding to its object in use are appropriately compounded thereby providing these compositions as fragrant cosmetics, health and sanitary materials or medicaments. Specifically, the clathrate compound of the present invention can be compounded in, for example, skin cosmetics, shampoos, rinses, fragrances, colognes, hair tonics, hair cosmetics including hair creams, bath agents, soaps, detergents, softeners, room fragrances, furniture cares, disinfectants, insecticides, bleaching agents, dental creams, oral detergents, or ointments. It is preferably used, particularly, for preparations, such as lotions for all body, oral detergents and shampoos, which use water as a major component and preparations, such as bath agents, which is used by dissolving in water, these preparations being shown in the examples described later.

DESCRIPTION OF THE PREFERRED EXAMPLES

The present invention will be explained in detail by way of examples and comparative examples which are not intended to be limiting of the present invention. The clathrate compounds (branched CD) used in the following examples are as follows:

(i) $G_1$-$\beta$-CD: glucosyl-$\beta$-cyclodextrin
(ii) $G_2$-$\beta$-CD: maltosyl-$\beta$-cyclodextrin
(iii) Isoeleat P (trademark): manufactured by Ensuiko Sugar Refining Co., Ltd., the amount of a branched $G_2$-CD: 50% or more, the ratio of $\alpha$-CD:$\beta$-CD:$\gamma$-CD=6:3:1.

The following instruments were used in the following measurements.

Nuclear magnetic resonance spectrum: $^1$H-NMR:AM-400 (400 MHz) (manufactured by Brucker Co., Ltd.)
Differential scanning calorimeter: DSC-50 (manufactured by Shimadzu Corporation)
UV-ray absorption spectrum (UV): UV-260 (manufactured by Shimadzu Corporation)

EXAMPLE 1
(Preparation of a $G_1$-$\beta$-CD Clathrate Compound of Hinokitiol)

To 3.6 g (2.78 mmol) of a $G_1$-$\beta$-CD (manufactured by Ensuiko Sugar Refining Co., Ltd.) which was dissolved in 12 ml of water was added a solution produced by dissolving 0.4 g (2.44 mmol, the ratio to the CD: 11.1% by weight) of a hinokitiol (manufactured by Takasago International Corporation) in 8 ml of acetone. The mixture was stirred at 35° C. for about one hour and acetone was then distilled under reduced pressure to obtain a transparent solution. The resulting solution was treated for one minute in an ultrasonic homogenizer (manufactured by Kaijo Electric Corporation; 0.8 A; frequency: 38 KHz) and was then allowed to stand in a refrigerator at 10° C. all night. The solution made cloudy was freeze-dried and then powdered in a mortar to obtain 3.90 g of the object branched CD clathrate compound of hinokitiol as a white powder.

The resulting clathrate compound was subjected to the measurements of the proton nuclear magnetic resonance spectrum ($^1$H-NMR)(solvent: deuterated dimethyl sulfoxide [(CD$_3$)$_2$SO] and UV-ray absorption spectrum (241 nm) with respect to its aqueous solution. As a result, it was confirmed that the mol ratio of $G_1$-$\beta$-CD:hinokitiol of this compound was about 1:0.93 (a hinokitiol was contained in an amount of 105 mg/1000 mg).

In order to confirm that the resulting compound was not a simple mixture but formed a clathrate, a mixture of a $G_1$-$\beta$-CD and a hinokitiol which were mixed in a ratio by weight of 1:9 was formed. Four samples consisting of the above mixture, a hinokitiol, a $G_1$-$\beta$-CD and the above resulting compound were subjected to a differential thermal analysis. FIGS. 1 to 4 show the results of the analysis when the temperature was raised at a rate of 10° C. per minute. FIGS. 1 to 4 are the graphs of the differential thermal analysis (DSC:±4 mcal/sec) of the hinokitiol, $G_1$-$\beta$-CD, mixture of $G_1$-$\beta$-CD and a hinokitiol blended in a ratio by weight of 1:9 and the compound prepared in this example respectively.

Figure 3:
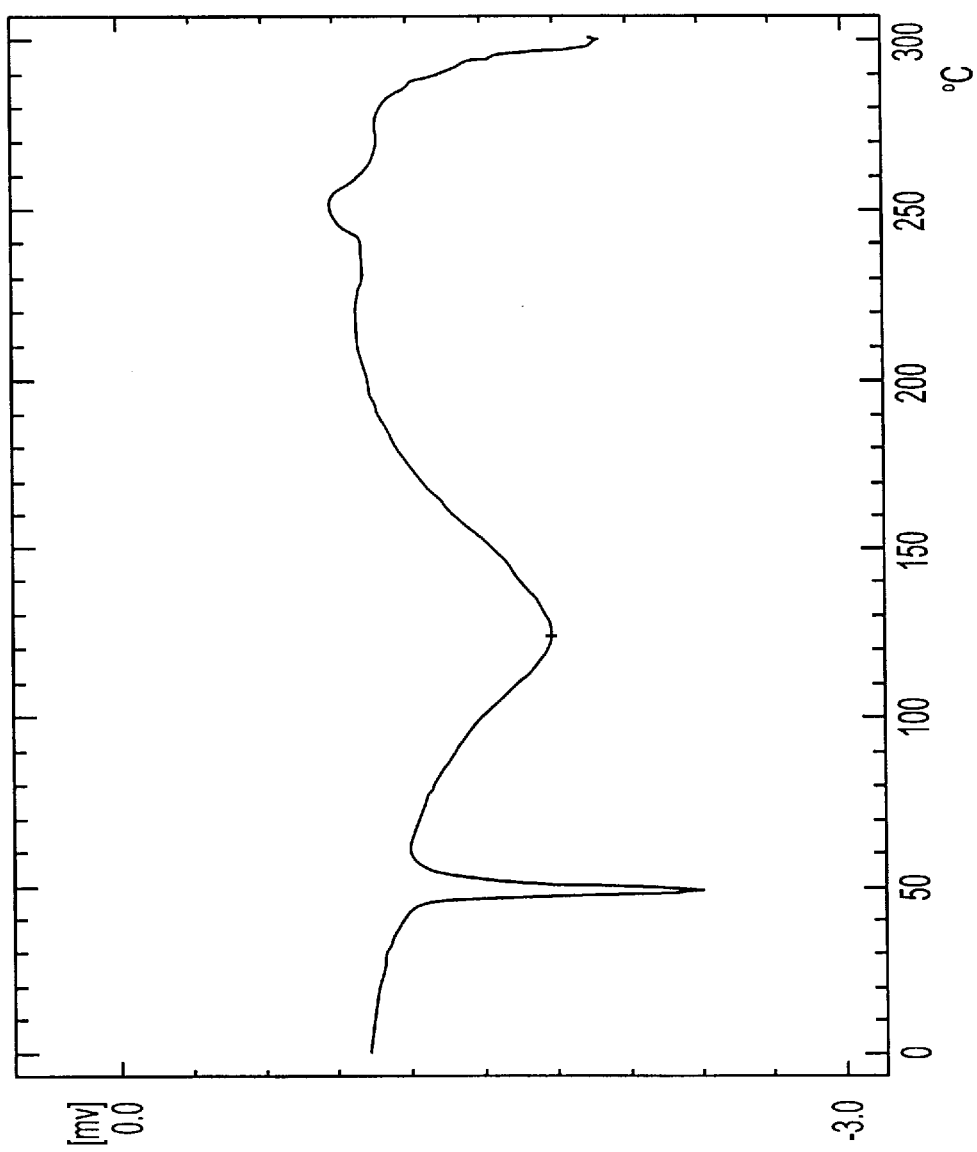
FIG. 3 is an analysis graph showing the result of a differential thermal analysis of a mixture of a $G_1$-β-CD and a hinokitiol which are blended at a ratio by weight of 1:9.
Figure 4:
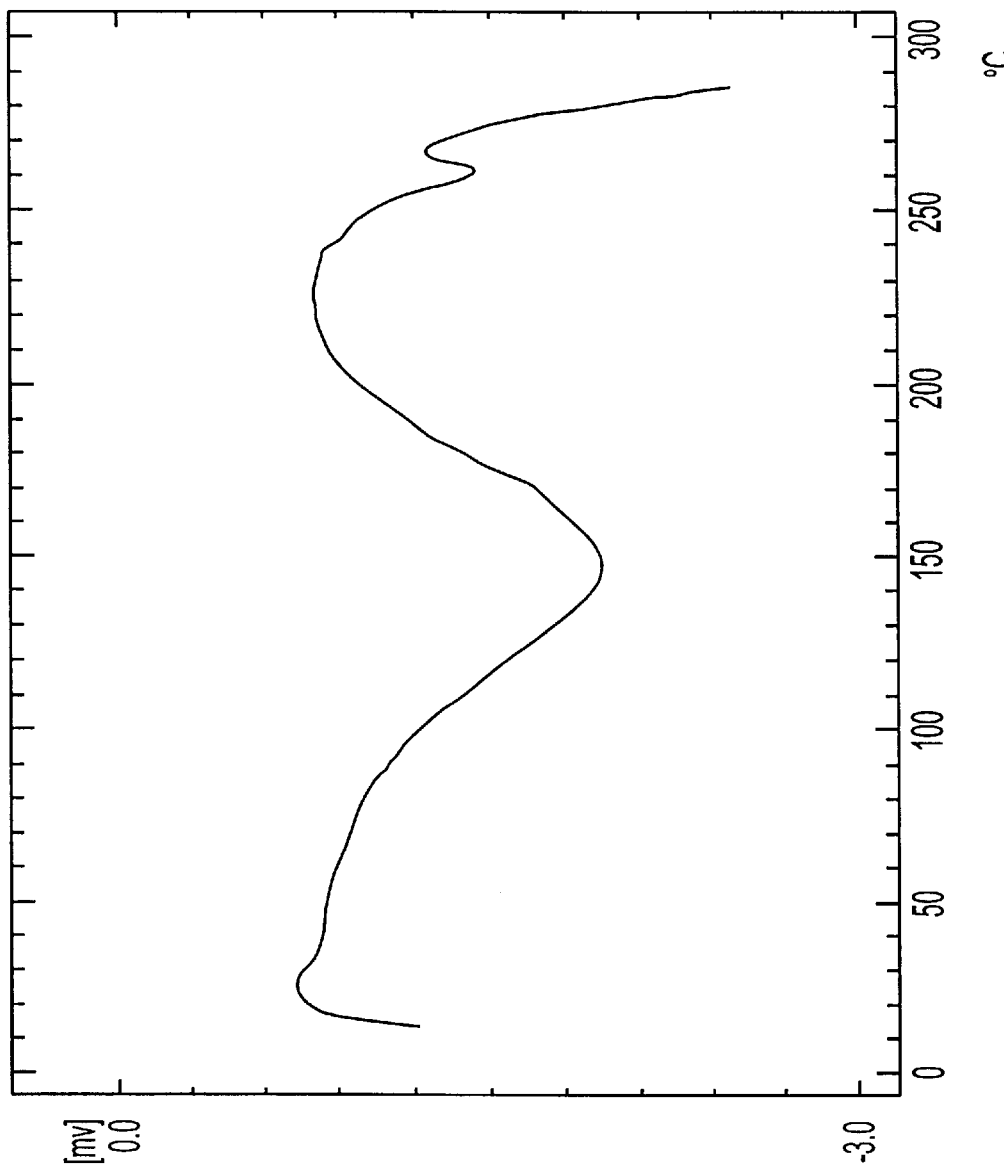
FIG. 4 is an analysis graph showing the result of a differential thermal analysis of a compound prepared in Example 1.

Comparing FIGS. 1 to 4, the endothermic peak of the hinokitiol is observed in FIG. 3, but is not observed at all in FIG. 4. Therefore, it is confirmed that, in the compound of this example, the $G_1$-$\beta$-CD and the hinokitiol form a clathrate.

Figures 5A, 5B:
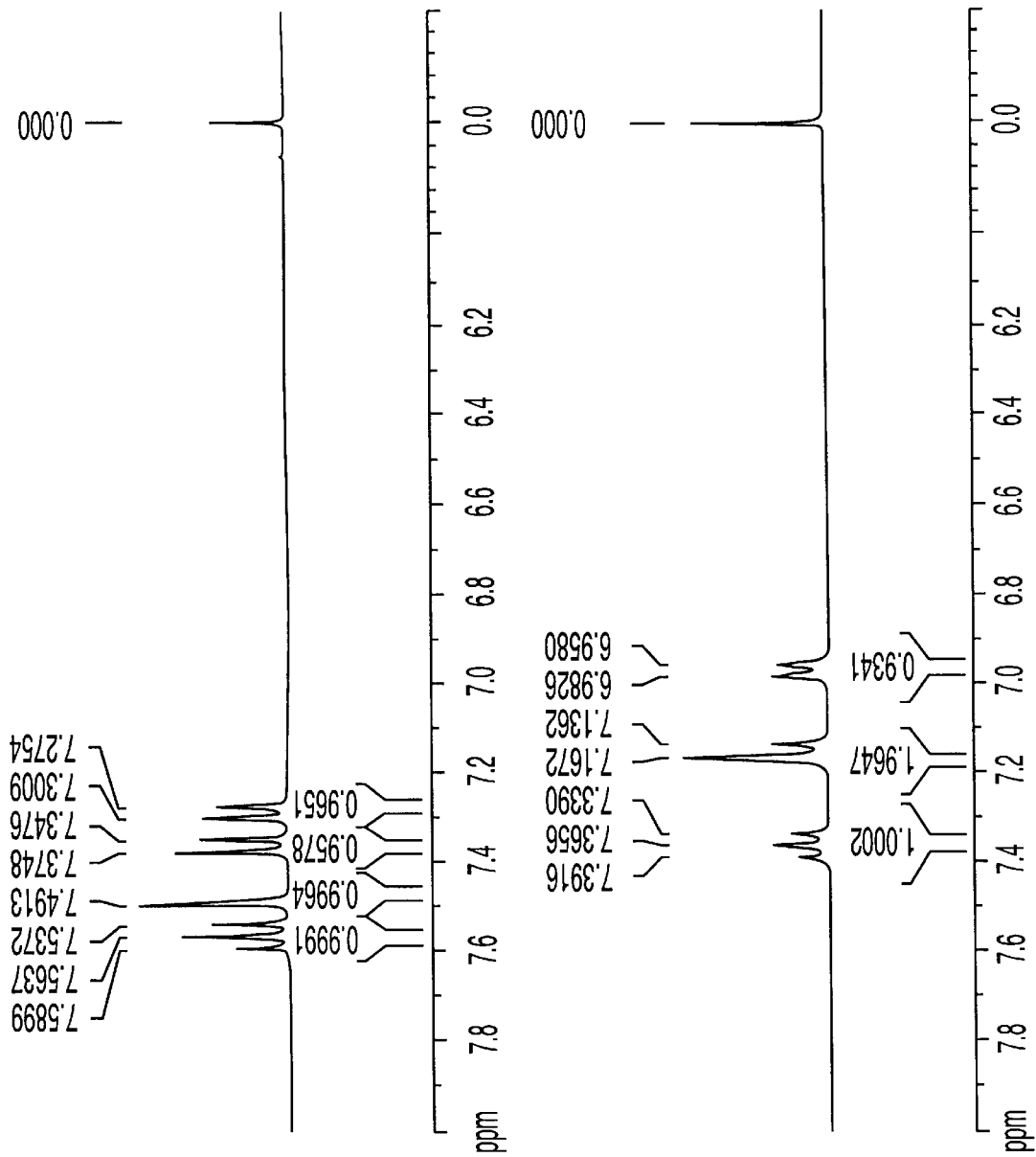
FIG. 5(A) shows the $^1$H-NMR spectrum of a hinokitiol at the aromatic ring region and FIG. 5(B) shows the $^1$H-NMR spectrum of a compound prepared in Example 1.

FIG. 5 shows the $^1$H-NMR spectrums (heavy water solution) of (A) the hinokitiol and of (B) the compound of this example, namely, the clathrate compound of the $G_1$-$\beta$-CD and hinokitiol at the aromatic ring region of a hinokitiol by using tetramethylsilane (TMS) as the external standard. The difference between the spectrums of (A) and (B) is due to the clathration by the $G_1$-$\beta$-CD. The measurement of $^1$H-NMR of a substance containing a clathrate material extracted by an organic solvent from a solution of the above clathrate compound showed that the substance exhibited the same spectrum pattern as a hinokitiol. From this result, it was confirmed that a hinokitiol formed a clathrate, for instance, without being resolved.

EXAMPLE 2
(Preparation of a $G_2$-$\beta$-CD Clathrate Compound of Hinokitiol)

3.6 g (2.47 mmol) of a $G_2$-$\beta$-CD (manufactured by Ensuiko Sugar Refining Co., Ltd.) was dissolved with stirring in 12 ml of water. To the mixed solution was added a solution produced by dissolving 0.4 g (2.44 mmol, 0.99 molar equivalents, the ratio to the CD: 11.1% by weight) of a hinokitiol in 8 ml of acetone. The mixture was stirred at 35° C. for about one hour and acetone was then distilled under reduced pressure to obtain a transparent solution. The resulting solution was treated in the same manner as in Example 1 to obtain 3.95 g of a dry clathrate compound of a white color. The amount of a hinokitiol in the clathrate compound was measured by means of an absorption spectrum in a UV range (241 nm) using an aqueous solution containing the clathrate compound. The measurement showed that a clathrate compound containing a hinokitiol in a ratio by mol of 1:0.71 (a hinokitiol is contained in an amount of 74 mg/1000 mg) was produced.

EXAMPLE 3
(Preparation of a $G_1$-β-CD Clathrate Compound of a Sodium Salt of Hinokitiol)

3.6 g (2.47 mmol) of a $G_1$-β-CD was dissolved with stirring in 12 ml of water. To the mixed solution was added a solution produced by dissolving 0.4 g (2.15 mmol, 0.77 molar equivalents, the ratio to the CD: 11.1% by weight) of a sodium salt of hinokitiol. The mixture was stirred at 35° C. for about one hour and acetone was then distilled under reduced pressure to obtain a transparent solution. The resulting solution was successively treated in the same manner as in Example 1 to obtain 3.86 g of a dry clathrate compound of a slightly yellowish white color. The amount of a sodium salt of hinokitiol in the clathrate compound was measured by means of an absorption spectrum in a UV range (244 nm) using an aqueous solution containing the clathrate compound. The measurement showed that a clathrate compound containing a sodium salt of hinokitiol in a ratio by mol of 1:0.62 (a sodium salt of hinokitiol is contained in an amount of 80 mg/1000 mg) was produced.

EXAMPLE 4
(Preparation of an Isoeleat P Clathrate Compound of Hinokitiol)

3.6 g of an Isoeleat P (manufactured by Ensuiko Sugar Refining Co., Ltd., the amount of a branched CD: 50% or more, the ratio of α-CD:β-CD:γ-CD=6:3:1) was dissolved with stirring in 12 ml of water. To the mixed solution was added a solution produced by dissolving 0.4 g (2.44 mmol, the ratio to the CD: 11.1% by weight) of ahinokitiol in 8 ml of acetone. The mixture was stirred at 35° C. for about one hour and acetone was then distilled under reduced pressure to obtain a transparent solution. The resulting solution was successively treated in the same manner as in Example 1 to obtain 3.72 g of a dry clathrate compound of a white color. The amount of a hinokitiol in the clathrate compound was measured by means of an absorption spectrum in a UV range (244 nm) using an aqueous solution containing the clathrate compound. The measurement showed that a clathrate compound containing a hinokitiol in a ratio by weight of 1:0.03 (a hinokitiol is contained in an amount of 30 mg/1000 mg) was produced.

Reference Example 1
(Preparation of a β-CD Clathrate Compound of Hinokitiol)

To 4.56 g (4.0 mmol) of a β-CD (manufactured by Nippon Food Industrial Co., Ltd.) which was dissolved in 70 ml of water at 30° C. was added a solution produced by dissolving 0.66 g (4.0 mmol) of a hinokitiol in 16 ml of acetone. The mixture was heated to about 50° C. and was stirred for about one hour to obtain a transparent solution. The resulting solution was treated for one minute in a homogenizer (manufactured by Kaijo Electric Corporation; 0.8 A; frequency: 38 KHz) and was then allowed to stand in a refrigerator at 10° C. all night. The solution made cloudy was added to 300 ml of acetone whose temperature was −35° C. and the resulting solution was mixed with stirring. Next, suction filtration was carried out immediately to separate and collect a white crystal, which was then dried under reduced pressure for 8 hours in a vacuum desiccator. The resulting clathrate compound was powdered in a mortar to obtain 4.69 g of the object β-CD clathrate compound of hinokitiol. The resulting clathrate compound was subjected to the measurements of the proton nuclear magnetic resonance spectrum ($^1$H-NMR)(solvent: deuterated dimethyl sulfoxide [$(CD_3)_2SO$] and UV-ray absorption spectrum (245 nm) with respect to its aqueous solution. As a result, it was confirmed that the mol ratio of β-CD:hinokitiol of this compound was about 1:0.90 (a hinokitiol was contained in an amount of 115 mg/1000 mg).

The solubilities of the above various branched CD clathrate compounds prepared in the above examples and reference example in water at 15° C. are shown in Table 1.

TABLE 1

| Hinokitiols | % |
| --- | --- |
| Hinokitiol | <0.05 |
| β-CD clathrate compound of hinokitiol | 0.3 |
| $G_1$-β-CD clathrate compound of hinokitiol prepared in Example 1 | 15.0 |
| $G_2$-β-CD clathrate compound of hinokitiol prepared in Example 2 | 47.5 |
| Isoeleat P clathrate compound of hinokitiol prepared in Example 4 | 24.7 |

Test Example 1
(Evaluation of the Corrosion Resistance of a Hinokitiol)

Test pieces made of stainless were placed in each aqueous solution of a hinokitiol, a sodium salt of hinokitiol and the $G_1$-β-CD clathrate compound of a hinokitiol obtained in Example 1. These aqueous solutions were stirred in the same condition at room temperature (25° C.) and 90° C. to inspect the corrosion of stainless. The results are shown in Table 2.

Test panel
  Sus-316L (manufactured by Nippon Test Panel Industries Co., Ltd.); and
  Sus-304 (manufactured by Nippon Test Panel Industries Co., Ltd.).

Consequently, as shown in Table 2, in the condition of room temperature, Sus-316L and Sus-304 (stainless test piece) were reduced in thickness by 0.57 mm/year and 0.67 mm/year respectively in an aqueous 0.1% solution of the hinokitiol whereas Sus-316L and Sus-304 (stainless test piece) were reduced in thickness by 0.05 mm/year and 0.10 mm/year respectively in an aqueous 0.1% solution of the sodium salt of hinokitiol. By using a sodium salt of hinokitiol, the corrosion could be reduced to about one-tenth that of a hinokitiol. Moreover, in the case of using the clathrate compound of the present invention, Sus-316L and Sus-304 (stainless test piece) were reduced in thickness by 0.01 mm/year and 0.03 mm/year respectively in an aqueous 1.0% solution of the clathrate compound at room temperature.

TABLE 2

| | Material | |
| --- | --- | --- |
| Corrosion rate at 25° C. (mm/year) | Sus 316L | Sus 304 |
| 0.1% aqueous solution of hinokitiol | 0.57 mm | 0.67 mm |
| 0.1% aqueous solution of sodium salt of hinokitiol | 0.05 mm | 0.10 mm |
| 1.0% aqueous solution of clathrate of hinokitiol prepared in Example 1 | 0.01 mm | 0.03 mm |

Next, as shown in Table 3, in the condition of a temperature of 90° C., Sus-316L and Sus-304 (stainless test piece) were reduced in thickness by 1.96 mm/year and 3.27 mm/year respectively in an aqueous 0.1% solution of the hinokitiol whereas Sus-316L and Sus-304 (stainless test piece) were reduced in thickness by 0.15 mm/year and 0.30 mm/year respectively in an aqueous 0.1% solution of the sodium salt of hinokitiol. Moreover, in the case of using the clathrate compound of the present invention, Sus-316L and Sus-304 (stainless test pieces) were reduced in thickness by 0.05 mm/year and 0.08 mm/year respectively in an aqueous 1.0% solution of the clathrate compound. By using the $G_1$-β-CD of hinokitiol, no production of rust was observed and it was thus clarified that a corrosion to stainless could be greatly reduced.

TABLE 3

|  | Material | |
| --- | --- | --- |
| Corrosion rate at 90° C. (mm/year) | Sus 316L | Sus 304 |
| 0.1% aqueous solution of hinokitiol | 1.96 mm | 3.27 mm |
| 0.1% aqueous solution of sodium salt of hinokitiol | 0.15 mm | 0.30 mm |
| 1.0% aqueous solution of clathrate of hinokitiol prepared in Example 1 | 0.05 mm | 0.08 mm |

Test Example 2
(Evaluation of the Heat Stability (Sublimation) of a Hinokitiol)

1000 mg of each of a hinokitiol, a sodium salt of hinokitiol, the $G_1$-β-CD clathrate of hinokitiol prepared in Example 1, the $G_2$-β-CD clathrate of hinokitiol prepared in Example 2 and the Isoeleat P clathrate of hinokitiol prepared in Example 4 were allowed to stand at 90° C. for 20 hours to measure the residual weight. The results of the residual weight, sublimation rate (%) and sublimation rate (%) converted into a hinokitiol were shown in Table 4.

As shown in Table 4, it was confirmed that the hinokitiol was sublimated in an amount of 99.2% and even the sodium salt of hinokitiol was sublimated in an amount of 23.6%. On the other hand, the sublimation of each branched CD clathrate was significantly restrained. Particularly, the sublimation rate of the $G_1$-β-CD clathrate was 0.4% and when it was converted into the sublimation rate of a hinokitiol, it was confirmed that the sublimation rate of a hinokitiol was reduced to 4.3%. Specifically, it was confirmed that the sublimation of a hinokitiol, if it was made into a branched CD clathrate, can be prevented and a reduction in the amount of a hinokitiol due to sublimation can be restrained more significantly than in the case of a hinokitiol or alkaline metal salts.

TABLE 4

| Hinokitiols | Residual weight (mg) | Sublimation rate (%) (Converted into hinokitiol) |
| --- | --- | --- |
| Hinokitiol | 8 | 99.2 |
| Na salt of hinokitiol | 764 | 23.6 |
| $G_1$-β-CD clathrate of hinokitiol prepared in Example 1 | 996 | 0.4(4.3) |
| $G_2$-β-CD clathrate of hinokitiol prepared in Example 2 | 991 | 0.9(12.6) |
| Isoeleat P clathrate of hinokitiol prepared in Example 4 | 996 | 0.4(13.0) |

Test Example 3
(Test for Antibacterial Activity)

The clathrate compound of the present invention and non-clathrate compounds were each subjected to an antibacterial test. Aerobic and anaerobic bacteria used in the test are as follows:

Aerobic Bacteria
Sa: Staphylococcus aureus IAM 1011
Se: Staphylococcus epidermidis JCM 2414
Cm: Corynebacterium minutissiumum ATCC 23348
Ec: Escherichia coli IFO 3972
Sm: Serratia marcessenes IFO 3736
Pv: Proteus vulgaris IFO 3167
Mf: Malassezia furfur IFO 0656
Kp: Klebsiella pneumoniae IFO 13277
Cx: Corinebacterium xerosis JCM 1324
Anaerobic Bacteria
Pa: Propionibacterium acnes ATCC 12818
Fn: Fusobacterium nucleatum JCM 6328

The samples used in the antibacterial test are as follows in which butylparabene was used as a control compound. The concentrations of clathrate compounds were all measured by converting into the concentrations of a hinokitiol. Samples of antibacterial agents
1. Hinokitiol (Takasago International Corporation)
2. $G_1$-β-CD clathrate compound of hinokitiol (the compound of the present invention, described as "$G_1$-CD clathrate" in the tables)
3. Butylparabene (manufactured by Tokyo Chemical Industry Co., Ltd.)
Method: Serial Double Dilution Method As for the culture medium, an aqueous solution containing 38 g/l of a Muller-Hilton agar medium (manufactured by DEFCO) was used for aerobic bacteria and an aqueous solution containing 59 g/l of a GAM agar medium (manufactured by Nissui Pharmaceutical Co., Ltd.) for anaerobic bacteria. Each subject compound was added to each corresponding medium in a manner that the concentration of a hinokitiol was 400 μg/ml and diluted according to the serial double dilution method using the same medium. 10 ml of each resulting medium was poured into a plastic Schale with an inside diameter of 90 mm and was solidified. The solidified medium in the Schale was divided. 0.1 ml of a distilled water suspension containing the subject microorganisms (the number of microorganisms: $10^6$–$10^9$/ml) was inoculated into each compartment and incubated at 37° C. for 24 hours. The gross growth of each bacteria was observed to determine the minimal inhibitory concentration (MIC, μg/ml) which inhibited the growth of microorganisms. The results are shown in Tables 5 and 6. Incidentally the incubation of anaerobic bacteria was performed using a gas pack jar for incubating anaerobic bacteria.

TABLE 5

|  | Se | Cm | Cx | Mf | Sa | Ec | Sm | Pv |
| --- | --- | --- | --- | --- | --- | --- | --- | --- |
| Hinokitiol | 50 | 50 | 50 | 50 | 50 | 50 | 200 | 50 |
| $G_{1\text{-CD clathrate}}$ | 50 | 25 | 50 | 25 | 50 | 25 | 200 | 25 |
| Butylparabene | 100 | 100 | 100 | 100 | 100 | 400 | >400 | 100 |

TABLE 6

|  | Kp | Pa | Fn |
| --- | --- | --- | --- |
| Hinokitiol | 50 | 100 | 100 |
| $G_1$-CD clathrate | 50 | 100 | 100 |
| Butylparabene | 100 | 200 | 100 |

As is clear from Tables 5 and 6, the clathrate compound of hinokitiol of the present invention possesses the same or higher antibacterial activity than a hinokitiol, showing that the clathration does not cause a reduction in the antibacterial activity.

EXAMPLE 5

(Antibacterial Agent)

5 parts by weight of the $G_1$-β-CD clathrate compound of hinokitiol prepared in Example 1 was dissolved in 95 parts by weight of distilled water to obtain a liquid antibacterial agent. This product as it is can be advantageously used as the antibacterial agent for antibacterial composition such as cosmetics and daily needs.

EXAMPLE 6

(Bath Agent)

Using the $G_1$-β-CD clathrate compound of hinokitiol prepared in Example 1, the following components were mixed according to a usual method to produce 100 g of a bath agent.

| Component | Proportion (% by weight) |
| --- | --- |
| $G_1$-β-CD clathrate compound of hinokitiol prepared in Example 1 | 0.5% |
| Sodium chloride | 10.0% |
| Silicic acid anhydride | 0.5% |
| Pigment | 0.001% |
| Perfume | 0.1% |
| Neutral sodium sulfate anhydride | Balance |

EXAMPLE 7

(Hair Lotion)

Using the $G_1$-β-CD clatrate compound of hinokitiol prepared in Example 1, the following components were mixed according to a usual method to produce 100 g of a hair lotion.

| Component | Proportion (% by weight) |
| --- | --- |
| $G_1$-β-CD clathrate compound of hinokitiol prepared in Example 1 | 2.0% |
| β-glycyrrhhetic acid | 0.2% |
| 1-menthol | 0.1% |
| Polyoxyethylene hydrogenated castor oil | 5.0% |
| BHT | 0.03% |
| Perfume | 0.05% |
| Purified water | Balance |

EXAMPLE 8

(Oral Detergent)

Using the $G_1$-β-CD clathrate compound of hinokitiol prepared in Example 1, the following components were mixed according to a usual method to produce 100 g of an oral detergent.

| Component | Proportion (% by weight) |
| --- | --- |
| $G_1$-α-CD clathrate compound of hinokitiol prepared in Example 1 | 1.0% |
| Ethanol | 12.5% |
| Sodium lauryl sulfate | 1.25% |
| Glycerol | 10.0% |
| 1-menthol | 0.1% |
| Saccharin | 0.001% |
| Pigment | 0.003% |
| Perfume | 0.05% |
| Purified water | Balance |

EXAMPLE 9

(Lotion)

Using the $G_1$-β-CD clathrate compound of hinokitiol prepared in Example 1, the following components were mixed according to a usual method to produce 100 g of a lotion.

| Component | Proportion (% by weight) |
| --- | --- |
| $G_1$-β-CD clathrate compound of hinokitiol prepared in Example 1 | 2.0% |
| Loofah extract liquid | 2.0% |
| 1,3-butylene glycol | 5.0% |
| Sodium citrate | 0.1% |
| Ethanol | 15.0% |
| Pigment | 0.0005% |
| Perfume | 0.05% |
| Purified water | Balance |

EXAMPLE 10

(Shampoo)

Using the $G_1$-β-CD clathrate compound of hinokitiol prepared in Example 1, the following components were mixed according to a usual method to produce 100 g of a shampoo composition.

| Component | Proportion (% by weight) |
| --- | --- |
| $G_1$β-CD clathrate compound of hinokitiol prepared in Example 1 | 1.0% |
| Decanoic acid | 0.05% |
| Triethanolamine lauryl sulfate | 18.5% |
| Hydroxypropylmethyl cellulose | 15.0% |
| Ammonium lauryl sulfate | 8.0% |
| Cocamide | 4.0% |
| Palmitic acid | 0.3% |
| 1,3-dimethylol-5,5-dimethylhydantoin | 0.15% |
| Disodium ethylenediamine tetraacetate | 0.05% |
| Citric acid | Trace |
| Common salt | Trace |
| Perfume | 0.07% |
| Purified water | Balance |

EXAMPLE 11

(Detergent)

Using the $G_1$-β-CD clathrate compound of hinokitiol prepared in Example 1, the following components were mixed according to a usual method to produce 100 g of a detergent.

| Component | Proportion (% by weight) |
| --- | --- |
| G₁β-CD clathrate compound of hinokitiol prepared in Example 1 | 2.0% |
| Senecioic acid | 0.1% |
| White vaseline | 6.0% |
| Alkylallyl polyether sulfonate | 50.0% |
| Cholesterol | 2.0% |
| Perfume | 0.1% |
| Purified water | Balance |

Comparative Example 1

(Hair Lotion)

Using the β-CD clathrate compound of hinokitiol prepared in Reference Example 1, the following components were mixed in the same manner as in Example 7 to produce a hair lotion.

| Component | Proportion (% by weight) |
| --- | --- |
| β-CD clathrate compound of hinokitiol prepared in Reference Example 1 | 2.0% |
| β-glycyrrhhetic acid | 0.2% |
| 1-menthol | 0.1% |
| Polyoxyethylene hydrogenated castor oil | 5.0% |
| BHT | 0.03% |
| Perfume | 0.05% |
| Purified water | Balance |

This product was a white suspension and produced a white precipitate when it was allowed to stand at room temperature with the result that it was unsuitable for the use as the hair lotion.

Comparative Example 2

(Oral Detergent)

Using the β-CD clathrate compound of hinokitiol prepared in Reference Example 1, the following components were mixed in the same manner as in Example 8 to produce an oral detergent.

| Component | Proportion (% by weight) |
| --- | --- |
| β-CD clathrate compound of hinokitiol prepared in Reference Example 1 | 1.0% |
| Ethanol | 12.5% |
| Sodium lauryl sulfate | 1.25% |
| Glycerol | 10.0% |
| 1-menthol | 0.1% |
| Saccharin | 0.001% |
| Pigment | 0.003% |
| Perfume | 0.05% |
| Purified water | Balance |

This product was a white suspension and produced a white precipitate when it was allowed to stand at room temperature with the result that it was unsuitable for the use as the oral detergent.

Comparative Example 3

(Lotion)

Using the β-CD clathrate compound of hinokitiol prepared in Reference Example 1, the following components were mixed in the same manner as in Example 9 to produce a lotion.

| Component | Proportion (% by weight) |
| --- | --- |
| β-CD clathrate compound of hinokitiol prepared in Reference Example 1 | 2.0% |
| Loofah extract liquid | 2.0% |
| 1,3-butylene glycol | 5.0% |
| Sodium citrate | 0.1% |
| Ethanol | 15.0% |
| Pigment | 0.005% |
| Perfume | 0.05% |
| Purified water | Balance |

This product was a white suspension and produced a white precipitate when it was allowed to stand at room temperature with the result that it was unsuitable for the use as the lotion.

Comparative Example 4

(Shampoo)

Using the β-CD clathrate compound of hinokitiol prepared in Reference Example 1, the following components were mixed in the same manner as in Example 10 to produce a shampoo composition.

| Component | Proportion (% by weight) |
| --- | --- |
| β-CD clathrate compound of hinokitiol prepared in Reference Example 1 | 1.0% |
| Decanoic acid | 0.05% |
| Triethanolamine lauryl sulfate | 18.5% |
| Hydroxypropylmethyl cellulose | 15.0% |
| Ammonium lauryl sulfate | 8.0% |
| Cocamide | 4.0% |
| Palmitic acid | 0.3% |
| 1,3-dimethylol-5,5-dimethylhydantoin | 0.15% |
| Disodium ethylenediamine tetraacetate | 0.05% |
| Citric acid | Trace |
| Common salt | Trace |
| Perfume | 0.07% |
| Purified water | Balance |

This product was a white suspension and produced a white precipitate when it was allowed to stand at room temperature with the result that it was unsuitable for the use as the shampoo.

Comparative Example 5

(Detergent)

Using the β-CD clathrate compound of hinokitiol prepared in Reference Example 1, the following components were mixed in the same manner as in Example 11 to produce a detergent.

| Component | Proportion (% by weight) |
| --- | --- |
| β-CD clathrate compound of hinokitiol prepared in Reference Example 1 | 2.0% |
| Senecioic acid | 0.1% |

-continued

| Component | Proportion (% by weight) |
|---|---|
| White vaseline | 6.0% |
| Alkylallyl polyether sulfonate | 50.0% |
| Cholesterol | 2.0% |
| Perfume | 0.1% |
| Purified water | Balance |

This product was a white suspension and produced a white precipitate when it was allowed to stand at room temperature with the result that it was unsuitable for the use as the detergent.

Test Example 4
(Comparative Test for Antibacterial Activity)

Solutions of the hair lotions prepared in Example 7 and Comparative Example 1 respectively, solutions of the oral detergents prepared in Example 8 and Comparative Example 2 respectively, solutions of the lotions prepared in Example 9 and Comparative Example 3 respectively, solutions of the shampoos prepared in Example 10 and Comparative Example 4 respectively and solutions of the detergents prepared in Example 11 and Comparative Example 5 respectively were subjected to a test for antibacterial activity against staphylococcus aureus (Sa).

Sa: Staphylococcus aureus IAM 1011

Method: Like Test Example 3, as for the culture medium, an aqueous solution containing 38 g/l of a Muller-Hilton agar medium (manufactured by DEFCO) was used for aerobic bacteria. Each subject compound was added to each corresponding medium in a manner that the theoretical amount of a hinokitiol was 400 $\mu$g/ml and diluted according to the serial double dilution method using the same medium. 10 ml of each resulting medium was poured into a plastic Schale with an inside diameter of 90 mm and was solidified. The solidified medium in the Schale was divided. 0.1 ml of a distilled water suspension containing the subject microorganisms (the number of microorganisms: $10^6$–$10^9$/ml) was inoculated into each compartment and incubated at 37° C. for 24 hours. The gross growth of each bacteria was observed to determine the minimal inhibitory concentration (MIC, ppm) which inhibited the growth of microorganisms. The results are shown in Tables 7.

TABLE 7

| | |
|---|---|
| Hair lotion ($G_1$-$\beta$-CD clathrate) prepared in Example 7 | 100 |
| Hair lotion ($\beta$-CD clathrate) prepared in Comparative Example 1 | >400 |
| Oral detergent ($G_1$-$\beta$-CD clathrate) prepared in Example 8 | 100 |
| Oral detergent ($\beta$-CD clathrate) prepared in Comparative Example 2 | >400 |
| Lotion ($G_1$-$\beta$-CD clathrate) prepared in Example 9 | 100 |
| Lotion ($\beta$-CD clathrate) prepared in Comparative Example 3 | >400 |
| Shampoo ($G_1$-$\beta$-CD clathrate) prepared in Example 10 | 100 |
| Shampoo ($\beta$-CD clathrate) prepared in Comparative Example 4 | >400 |
| Detergent ($G_1$-$\beta$-CD clathrate) prepared in Example 11 | 100 |
| Detergent ($\beta$-CD clathrate) prepared in Comparative Example 5 | >400 |

Making a comparison between the antibacterial activities of Examples 7 to 11 in which the branched CD clathrate was formulated and the antibacterial activities of Comparative Examples 1 to 5 in which the disbranched CD was formulated, the following fact is clarified from Table 7. Specifically, all of the products of Comparative Examples 1 to 5 in which the disbranched CD was formulated had a minimal inhibitory concentration exceeding 400 ppm, showing that the antibacterial activity of a hinokitiol was reduced. On the other hand, all of the products of Examples 7 to 11 in which the branched CD clathrate was formulated had a minimal inhibitory concentration as low as 100 ppm, showing that they maintained high antibacterial activities.

As is evident from the above descriptions, according to the present invention in which a hinokitiol is formed into a branched cyclodextrin clathrate, the antibacterial activity of the hinokitiol is not damaged, its heat stability is made high, the corrosion to metals is inhibited and the solubility in water can be significantly improved. Therefore, the clathrate compound of the present invention, as an antibacterial agent having high water-solubility, is suitable for the purpose intended to impart an antibacterial activity to many products such as hair cosmetics, bath agents, skin cosmetics, detergents and oral compositions. Particularly when a branched $\beta$-cyclodextrin is used as the cyclodextrin, its effect is great.

What is claimed is:

1. A clathrate compound comprising a clathrate of a hinokitiol and a branched cyclodextrin wherein said compound has bactericidal activity of at least about twice the magnitude of a clathrated hinokitiol formed with unbranched cyclodextrins.

2. A clathrate compound according to claim 1, wherein the hinokitiol is at least one compound selected from the group consisting of hinokitiol and a metal salt of hinokitiol.

3. A clathrate compound according to claim 1 or 2, wherein the branched cyclodextrin is a branched $\beta$-cyclodextrin.

4. A clathrate compound according to claim 1 or 2, wherein the clathrate compound is a water-soluble powder.

5. A clathrate compound according to claim 3, wherein the clathrate compound is a water-soluble powder.

6. A composition comprising the clathrate compound according to claim 1 or 2 and a carrier or diluent.

7. A composition comprising the clathrate compound according to claim 3 and a carrier or diluent.

8. A composition comprising the clathrate compound according to claim 4 and a carrier or diluent.

9. A composition according to claim 6, wherein the composition comprising the clathrate compound has antibacterial activity,
    wherein the composition is a composition selected from the group consisting of a cosmetic composition, a bath agent, a detergent and an oral composition.

10. A clathrate compound according to claim 3, wherein the branched cyclodextrin is a branched $\beta$-cyclodextrin selected from the group consisting of a glucosyl $\beta$-cyclodextrin, a diglucosyl $\beta$-cyclodextrin, a maltosyl $\beta$-cyclodextrin, and a dimaltosyl $\beta$-cyclodextrin.

11. A clathrate compound according to claim 10, wherein the clathrate compound is a water-soluble powder.

12. A composition comprising the clathrate compound according to claim 10 and carrier or diluent.

13. A composition comprising the clathrate compound according to claim 11 and carrier or diluent.

14. A composition according to claim 12, wherein the composition comprising the clathrate compound has antibacterial activity,
    wherein the composition is a composition selected from the group consisting of a cosmetic composition, a bath agent, a detergent, and an oral composition.

* * * * *